(12) United States Patent
Wang et al.

(10) Patent No.: US 11,912,717 B2
(45) Date of Patent: Feb. 27, 2024

(54) CRYSTAL FORM OF TENVERMECTIN B, PREPARATION METHOD THEREFOR, AND USE THEREOF

(71) Applicant: Shenzhen Tenver Biopharm Co., Ltd., Guangdong (CN)

(72) Inventors: Jidong Wang, Zhejiang (CN); Jiansong Li, Zhejiang (CN); Hui Zhang, Zhejiang (CN); Lingjian Zhang, Zhejiang (CN); Jun Huang, Zhejiang (CN)

(73) Assignee: Shenzhen Tenver Biopharm Co., Ltd. (CN)

( * ) Notice: Subject to any disclaimer, the term of this patent is extended or adjusted under 35 U.S.C. 154(b) by 651 days.

(21) Appl. No.: 17/057,869

(22) PCT Filed: May 24, 2019

(86) PCT No.: PCT/CN2019/088333
§ 371 (c)(1),
(2) Date: Nov. 23, 2020

(87) PCT Pub. No.: WO2019/228260
PCT Pub. Date: Dec. 5, 2019

(65) Prior Publication Data
US 2021/0198274 A1    Jul. 1, 2021

(30) Foreign Application Priority Data
May 28, 2018    (CN) .......................... 201810521893.2

(51) Int. Cl.
*C07D 493/22*    (2006.01)
*A01N 43/90*    (2006.01)

(52) U.S. Cl.
CPC ........... *C07D 493/22* (2013.01); *A01N 43/90* (2013.01); *C07B 2200/13* (2013.01)

(58) Field of Classification Search
CPC ........................... C07B 2200/13; A01N 43/90
See application file for complete search history.

(56) References Cited

U.S. PATENT DOCUMENTS

| 2017/0013837 A1 | 1/2017 | Huang et al. |
| 2017/0127678 A1 | 5/2017 | Huang et al. |
| 2019/0116795 A1 | 4/2019 | Huang et al. |

(Continued)

FOREIGN PATENT DOCUMENTS

| CN | 104910228 A | 9/2015 |
| CN | 106167815 A | 11/2016 |
| CN | 107258798 A | 10/2017 |

(Continued)

OTHER PUBLICATIONS

Extended European Search Report including Written Opinion for Application No. 19812060.2 dated Feb. 15, 2022, pp. 1-8.

(Continued)

*Primary Examiner* — Shengjun Wang
(74) *Attorney, Agent, or Firm* — Lerner David LLP

(57) ABSTRACT

The present invention relates to a crystal form I of tenvermectin B, which can be characterized by X-ray powder diffraction (XRPD) pattern, Infrared (IR) absorption spectrum, Differential scanning calorimetry (DSC) thermogram and the like. Meanwhile, the present invention also relates to a method for preparing the crystal form I of tenvermectin B and a use thereof.

4 Claims, 3 Drawing Sheets

(56) References Cited

U.S. PATENT DOCUMENTS

2019/0151341 A1  5/2019  Wang et al.

FOREIGN PATENT DOCUMENTS

| CN | 107260751 A | 10/2017 |
|---|---|---|
| CN | 107513088 A | 12/2017 |
| CN | 110540556 A | 12/2019 |
| DE | 4031039 A1 | 4/1991 |
| EP | 0235085 A1 | 9/1987 |
| EP | 3118206 A1 | 1/2017 |
| WO | 2006060616 A1 | 6/2006 |
| WO | 2015135242 A1 | 9/2015 |
| WO | 2015135467 A1 | 9/2015 |
| WO | 2018177146 A1 | 10/2018 |

OTHER PUBLICATIONS

Pan, J. et al., "Three new milbemycins from a genetically engineered strain S. avermitilis MHJ1011", The Journal of Antibiotics, Sep. 2015, pp. 104-107, vol. 69. XP055371784.

Pikal, M. J. et al., "The stability of Insulin in Cristalline and Amorphous Solids: Observation of Greater Stability for the Amorphous Form", Pharmaceutical Research, Jun. 1997, pp. 1379-1387, vol. 14, No. 10. XP003023877.

Noriaki Hirayama, Ed., "Handbook of Organic Compound Crystal Preparation: Principles and Know-how", Maruzen, Jul. 25, 2008, 17 pgs.

Noriyuki Takata, "API Form Screening and Selection in Drug Discovery Stage", Pharm Stage, vol. 6, No. 10, Jan. 15, 2007, 9 pgs.

Decision of Refusal for Japanese Applicaiton No. 2021-517088 dated Jun. 28, 2022. 2 pgs.

International Search Report for Application No. PCT/CN2019/088333 dated Aug. 30, 2019, 2 pages.

2θ (°)

Wave number

CRYSTAL FORM OF TENVERMECTIN B, PREPARATION METHOD THEREFOR, AND USE THEREOF

CROSS-REFERENCE TO RELATED APPLICATIONS

The present application is a national phase entry under 35 U.S.C § 371 of International Application No. PCT/CN2019/ 088333 filed May 24, 2019, which claims priority from Chinese Application No. 201810521893.2 filed May 28, 2018, all of which are hereby incorporated herein by reference.

TECHNICAL FIELD

The present invention relates to the field of pharmaceuticals. More specifically, the present invention relates to a crystal form of tenvermectin B and a preparation method therefor and use thereof.

BACKGROUND

Sixteen-membered macrolides produced by streptomyces have high activity and broad spectrum activity. In addition, this kind of compounds is closely combined with soil in natural environment and is not easy to be washed and infiltrate. The compounds rapidly degrade into inactive compounds under light conditions or actions of soil microbes, and their molecular fragments are finally decomposed and utilized by plants and microbes as carbon sources without any residual toxicity. This kind of compounds has become a high-efficient biological pesticides used in agriculture and animals.

Due to remarkable properties of this kind of compounds, the homologues of the compounds have been extensively studied over the world. On one hand, molecular structure modification has been carried out by synthesis, and on the other hand, strains produced thereby are mutated by genetic improvement methods, in order to find new compounds with higher activity. A team of Zhejiang Hisun Pharmaceutical Co., Ltd. integrated Milbemycins PKS gene into the initial module of avermectins-producing strains *Streptomyces avermitilis* by a technology for seamless splicing large fragments of DNA, and obtained gene engineering strains MA220 for producing tenvermectins (see WO2015135242). Tenvermectin have main components: tenvermectin A and tenvermectin B (their structures are shown below). CN201410208660.9 and WO2015135467 disclose that tenvermectin A and tenvermectin B can control pests and mites of agricultural and forestry crops, such as *Tetranychus cinnabarinus, Tetranychus urticae, Plutella xylostella, Spodoptera exigua, Spodoptera litura*, cotton bollworm, *Agrotis ypsilon*, wireworm, armyworm, pine caterpillar, pine wood nematode and rice borer.

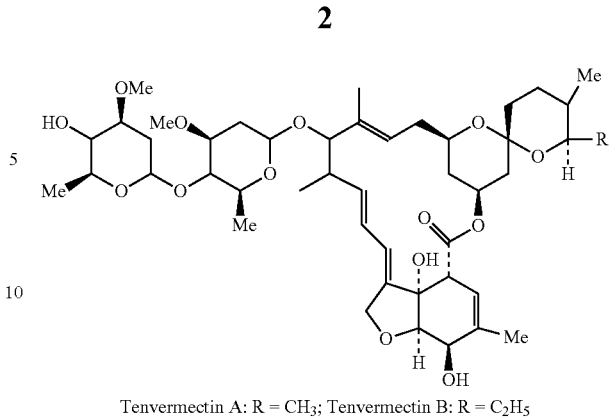

Tenvermectin A: R = $CH_3$; Tenvermectin B: R = $C_2H_5$

In addition, CN201410208660.9 and WO2015135467 also disclose a method for preparing tenvermectin A and B, wherein fermentation liquor of gene engineering strain MA220 is filtered with filter cloth to obtain a filter cake which is extracted with ethanol twice to obtain an ethanol extract; thus obtained ethanol extract is concentrated to dryness under vacuum, then separated by silica gel column chromatography, and then separated and purified by semi-preparative high-pressure liquid phase (eluent: methanol/acetonitrile/water=46/46/8), and thus obtained fractions are directly concentrated to dryness to obtain tenvermectin A and tenvermectin B. DE4031039 discloses a preparation method of tenvermectin B. According to the method, a crude product of tenvermectin B is synthesized, and then purified by silica gel (ethyl acetate/hexene=2:1) to obtain tenvermectin B. However, neither of the two preparation methods has studied the crystal form of the obtained tenvermectin B.

After a large number of experiments, firstly, the inventors of the present invention found that the product obtained according to the above two preparation methods is amorphous powder of tenvermectin B; secondly, during their study, the inventors found that the amorphous powder is very unstable, which leads to an increased cost for subsequent development of product. Finally, the inventors discovered a crystal form of tenvermectin B which is named as crystal form I. It is more stable and not easy to degrade, thus laying a solid foundation for the subsequent development of tenvermectin B.

SUMMARY

One object of the present invention is to provide a crystal form of tenvermectin B with good chemical and physical stability, which is named as crystal form I. The crystal form is more stable and not easy to degrade, and is more advantageous for the subsequent development of products.

The crystal form I of tenvermectin B according to the present invention exhibits characteristic peaks at 2θ degree of 9.62±0.20°, 11.33±0.20°, 11.79±0.20°, 12.48±0.20°, 13.48±0.20°, 21.12±0.20° and 23.70±0.20° in X-ray powder diffraction pattern using Cu-Kα radiation.

Preferably, the crystal form I of tenvermectin B according to the present invention further exhibits characteristic peaks at 2θ degree of 6.71±0.20°, 9.22±0.20°, 12.02±0.20°, 14.95±0.20°, 17.39±0.20°, 18.33±0.20°, 22.97±0.20°, 26.53±0.20° and 27.16±0.20° in X-ray powder diffraction pattern using Cu-Kα radiation.

More preferably, the crystal form I of tenvermectin B according to the present invention further exhibits characteristic peaks at 2θ degree of 4.63±0.20°, 15.45±0.20°, 15.80±0.20°, 16.64±0.20°, 17.74±0.20°, 19.20±0.20°, 19.75±0.20°, 22.14±0.20°, 22.52±0.20°, 25.01±0.20°, 25.54±0.20° and 29.60±0.20° in X-ray powder diffraction pattern using Cu-Kα radiation.

Furthermore, the 2θ degree at which the characteristic peaks are exhibited, d value and relative intensity data of the characteristic peaks shown in the X-ray powder diffraction pattern of the crystal form I of tenvermectin B according to the present invention are shown in table 1 below.

TABLE 1

2θ degree, d value and relative intensity of the crystal form I of tenvermectin B

| Peak No. | 2θ(°) | d (Interplanar spacing) | Relative intensity (%) |
|---|---|---|---|
| 1 | 4.63 | 19.0699 | 5.9 |
| 2 | 6.71 | 13.1625 | 29.7 |
| 3 | 9.22 | 9.5837 | 28.4 |
| 4 | 9.62 | 9.1862 | 100.0 |
| 5 | 11.33 | 7.8034 | 42.3 |
| 6 | 11.79 | 7.4998 | 43.8 |
| 7 | 12.02 | 7.3569 | 31.4 |
| 8 | 12.48 | 7.0867 | 49.7 |
| 9 | 13.48 | 6.5631 | 90.6 |
| 10 | 14.95 | 5.9209 | 34.0 |
| 11 | 15.45 | 5.7304 | 10.9 |
| 12 | 15.80 | 5.6043 | 14.0 |
| 13 | 16.64 | 5.3232 | 6.1 |
| 14 | 17.39 | 5.0953 | 26.6 |
| 15 | 17.74 | 4.9956 | 15.6 |
| 16 | 18.33 | 4.8360 | 29.4 |
| 17 | 19.20 | 4.6188 | 16.8 |
| 18 | 19.75 | 4.9515 | 12.5 |
| 19 | 21.12 | 4.2031 | 42.4 |
| 20 | 22.14 | 4.0117 | 18.5 |
| 21 | 22.52 | 3.9449 | 16.9 |
| 22 | 22.97 | 3.8686 | 20.4 |
| 23 | 23.70 | 3.7511 | 42.2 |
| 24 | 25.01 | 3.5575 | 11.5 |
| 25 | 25.54 | 3.4848 | 4.7 |
| 26 | 26.53 | 3.3570 | 22.4 |
| 27 | 27.16 | 3.2805 | 21.7 |
| 28 | 29.60 | 3.0154 | 10.5 |

The XRPD pattern of the crystal form I of tenvermectin B according to the present invention is shown in FIG. 1.

In addition, the crystal form I of tenvermectin B according to the present invention can be characterized by the infrared absorption spectrum measured by KBr pellet, and according to the spectrum, there are characteristic peaks at 3481 cm$^{-1}$, 2930 cm$^{-1}$, 1732 cm$^{-1}$, 1678 cm$^{-1}$, 1371 cm$^{-1}$, 1183 cm$^{-1}$, 1124 cm$^{-1}$, 984 cm$^{-1}$, 877 cm$^{-1}$ and 761 cm$^{-1}$.

The infrared spectrum of the crystal form I of tenvermectin B according to the present invention is shown in FIG. 2.

There is an exothermic peak at 160.8±2° C. in differential scanning calorimetry (DSC) thermogram of the crystal form I of tenvermectin B according to the present invention.

The DSC thermogram of the crystal form I of tenvermectin B according to the present invention is shown in FIG. 3.

The thermogravimetric analysis (TGA) thermogram of the crystal form I of tenvermectin B according to the present invention is shown in FIG. 4.

Another object of the present invention is to provide a method for preparing the crystal form I of tenvermectin B, which comprises a step of precipitating the crystal form I of tenvermectin B from a solvent system containing formamide.

Preferably, the solvent system containing formamide is a combination of lower alcohol, formamide and water or a combination of lower ketone, formamide and water, wherein the lower alcohol is preferably selected from a group consisting of methanol, ethanol or isopropanol; and the lower ketone is preferably acetone. More preferably, the solvent system containing formamide is preferably a combination of ethanol, formamide and water.

Preferably, the ratio of the mass of the tenvermectin B to the volume of the lower alcohol to the volume of formamide and to the volume of water is 1 g:2 ml:4-5 ml:2 ml, and the ratio of the mass of the tenvermectin B to the volume of the lower ketone to the volume of formamide and to the volume of water is 1 g:2 ml:4-5 ml:2 ml.

Preferably, the method for preparing the crystal form I of tenvermectin B according to the present invention comprises steps of: dissolving tenvermectin B with ethanol, then sequentially adding formamide and water thereto, stirring and crystallizing the thus obtained mixture to obtain the crystal form I of tenvermectin B, wherein, more preferably, the ratio of the mass of the tenvermectin B to the volume of ethanol to the volume of formamide to the volume of water is 1 g:2 ml:4-5 ml:2 ml.

Yet another object of the present invention is to provide a composition containing the crystal form I of tenvermectin B, which further comprises a pharmaceutically acceptable carrier, excipient or the combination thereof.

Yet another object of the present invention is to provide use of the crystal form I of tenvermectin B or the composition containing the crystal form I of tenvermectin B in preparing agents for controlling parasites and harmful insects. Objects to be controlled involve parasites and harmful insects in crops, humans, animals, aquatic products and the like. Reference can be made to CN201610213645.2 (use of tenvermectin for controlling parasites in human or animal) and CN201610211064.5 (use of tenvermectin for controlling harmful insects in agricultural and forestry crops).

The present invention also relates to use of raw materials containing the crystal form I of tenvermectin B in preparing preparation of anti-parasitic and preparation for controlling harmful insect. The preparation includes pour-on solution, tablet, injection and dry suspension.

In one embodiment, the tenvermectin B is dissolved with ethanol, then water is added thereto, and the amorphous powder of tenvermectin B is obtained by stirring and crystallizing. In another embodiment, the tenvermectin B is dissolved with ethanol, then formamide and water are added thereto in sequence, and the crystal form I of tenvermectin B is obtained by stirring and crystallizing. In yet another embodiment, the amorphous tenvermectin B is compared with the crystal form I of tenvermectin B regarding stability and it is found that the stability of the crystal form I of tenvermectin B is much better than that of amorphous tenvermectin B.

The crystal form I of tenvermectin B provided by the present invention is the only crystal form of tenvermectin B that is known now, and it is a significant breakthrough over prior art. Product of this crystal form has higher purity, and has more uniform crystal, subsequent drying process of the product is more controllable. In addition, the crystal transformation phenomenon does not occur and no degradation is found in the stability experiment of the product of this crystal form.

EMBODIMENTS

The following examples further illustrate the present invention, but do not limit the present invention.

Tenvermectin B raw material used in the present invention is prepared according to Example 1 in CN201410208660.9, and it is confirmed to be amorphous tenvermectin B by X-ray powder diffraction test.

The X-ray powder diffractometer and test conditions in the present invention are as follows. X-ray powder diffractometer model: Rigaku D/max-2200 Cu target; operation condition: scanning speed, 4°/min, scanning step width, 0.01°.

The infrared spectrophotometer and test conditions in the present invention are as follows. Infrared spectrophotometer model: BRWKER VECTOR 22; operation method: KBr pellet method, scanning range 400-4000 $cm^{-1}$.

The differential scanning calorimeter and test conditions are as follows. differential scanning calorimeter model: PERKIN ELMER DSC8000; operation condition: heating rate, 10° C./min, temperature range, 20° C.-280° C.

Thermal gravimetric analyzer and test conditions are as follows. thermal gravimetric analyzer model: PerkinElmer TGA400; operation condition: heating rate, 10° C./min, temperature range, 30° C.-300° C.

High performance liquid chromatograph (HPLC) and test conditions in the present invention are as follows. High performance liquid chromatograph, Agilent1100; Chromatographic column: C18, 4.6 mm×250 mm; mobile phase, acetonitrile:0.1% phosphoric acid aqueous solution=65:35 (v:v); Detection wavelength: 240 nm; flow rate, 1.0 ml/min; Column temperature: 25° C.

Unless otherwise specified, the dissolution and crystallization steps involved in the present invention generally require stirring, which can be carried out in known ways, such as magnetic stirring, mechanical stirring, etc.

Figure 1:
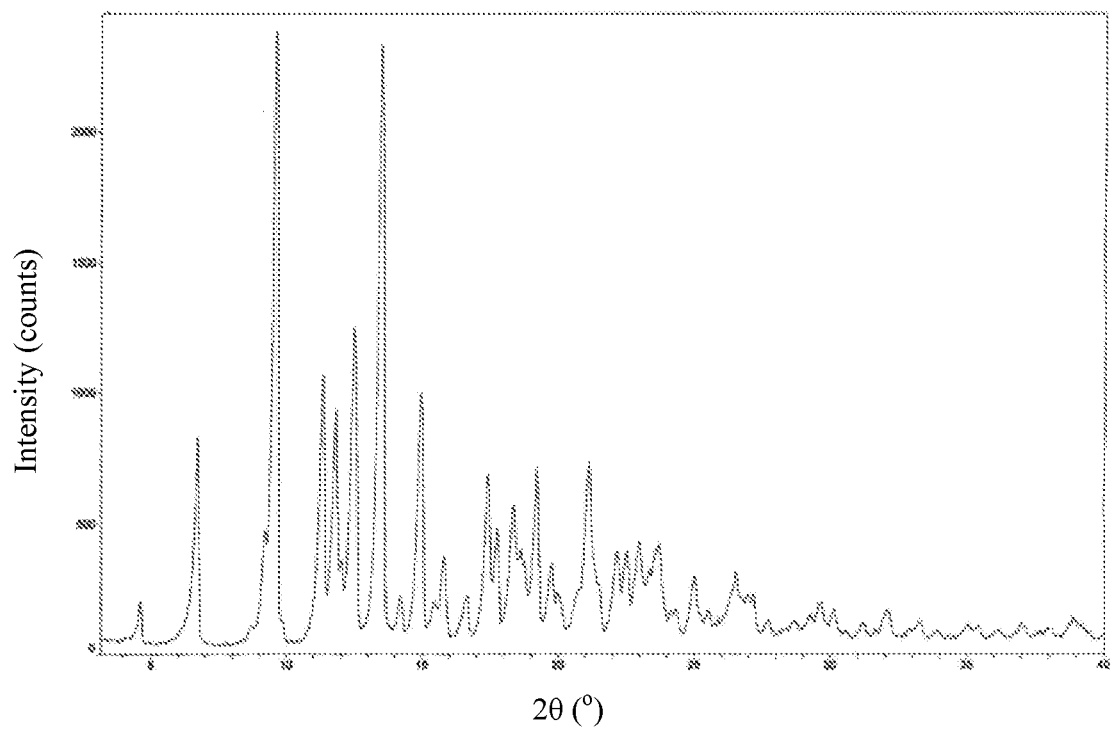
FIG. 1 is an X-ray powder diffraction pattern of the crystal form I of tenvermectin B obtained in Example 1.
Figure 2:
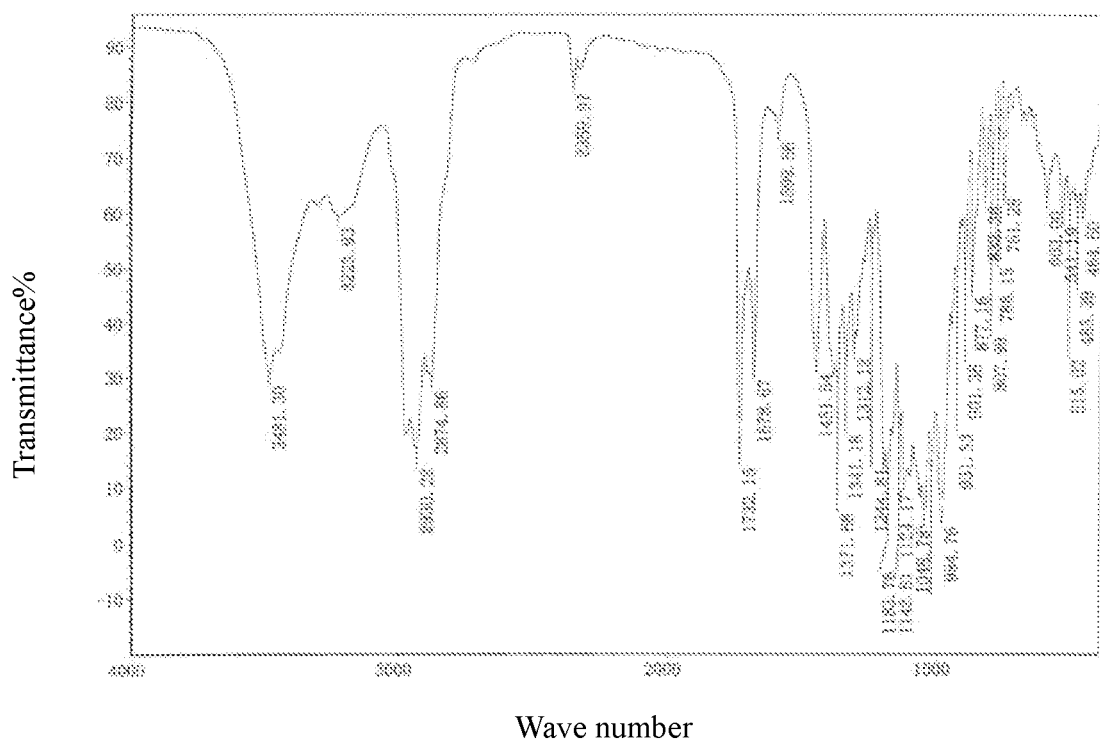
FIG. 2 is an infrared absorption spectrum of the crystal form I of tenvermectin B obtained in Example 1.
Figure 3:
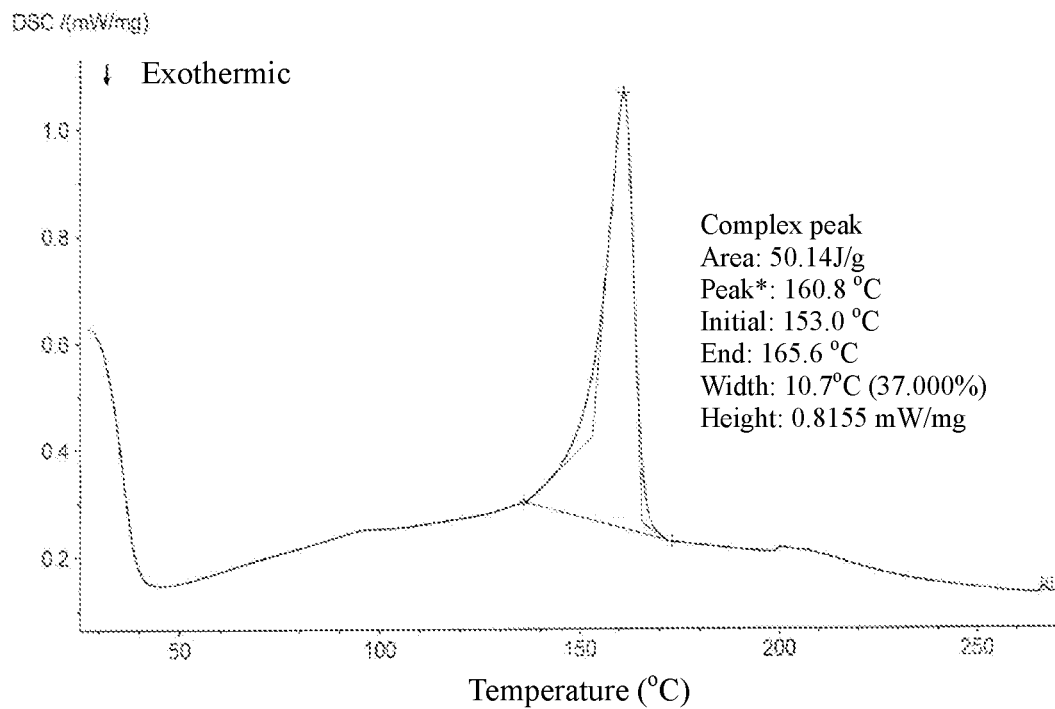
FIG. 3 is a DSC thermogram of the crystal form I of tenvermectin B obtained in Example 1.
Figure 4:
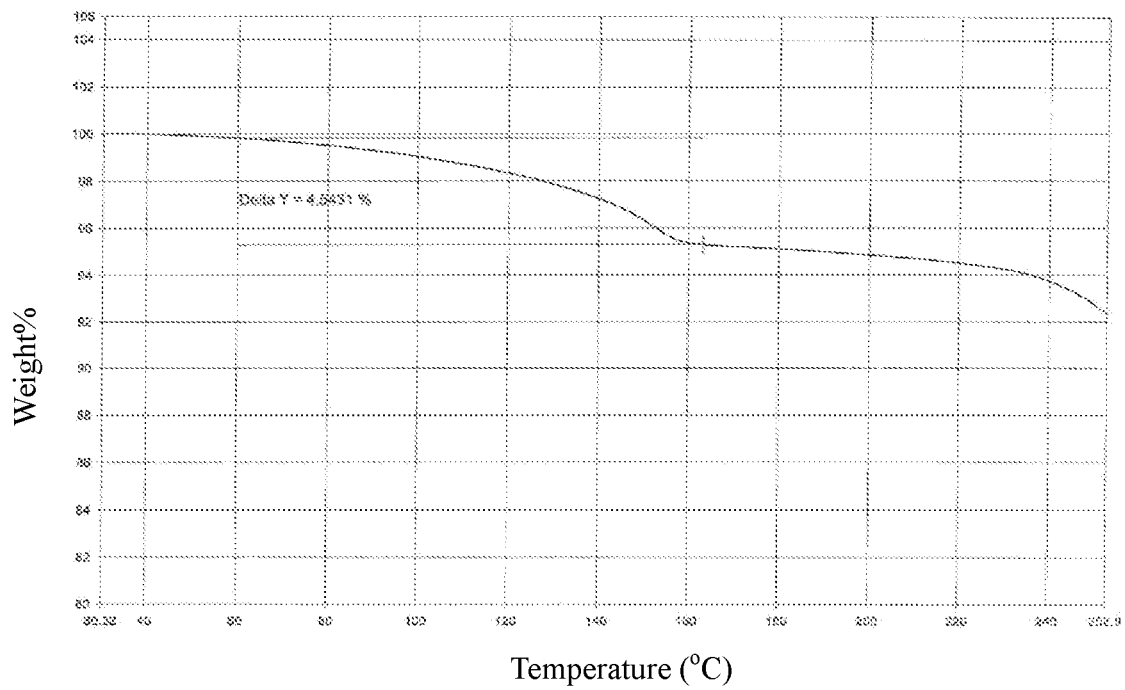
FIG. 4 is a TGA thermogram of the crystal form I of tenvermectin B obtained in Example 1.

Example 1: Preparation of Crystal Form I of Tenvermectin B 5.0 g of tenvermectin B raw material (purity 98.2% by HPLC) was dissolved in 10 ml of ethanol, and then filtered to obtain transparent filtrate. 25 ml of formamide and 10 ml of water were added thereto, thus obtained mixture was placed on a magnetic stirrer to stir at 200 r/min. After stirring at 25° C. for 10 h, the mixture was filtered to obtain a solid which was dried at 50° C. under vacuum for 48 h to obtain crystal form I of tenvermectin B (purity 99.1% by HPLC). The obtained product was sampled for testing. X-ray powder diffraction pattern was shown in FIG. 1, infrared absorption spectrum of the product was shown in FIG. 2, DSC thermogram of the product was shown in FIG. 3 and TGA thermogram of the product was shown in FIG. 4.

Example 2: Preparation of Crystal Form I of Tenvermectin B 5.0 g of tenvermectin B raw material (purity 98.2% by HPLC) was dissolved in 10 ml of acetone, and then filtered to obtain transparent filtrate. 20 ml of formamide and 10 ml of water were added thereto, thus obtained mixture was placed on a magnetic stirrer to stir at 200 r/min. After stirring at 25° C. for 10 h, the mixture was filtered to obtain a solid which was dried at 50° C. under vacuum for 48 h to obtain crystal form I of tenvermectin B (purity 98.8% by HPLC). The obtained product was sampled for testing. X-ray powder diffraction pattern confirmed that the product is crystal form I.

Figure 5:
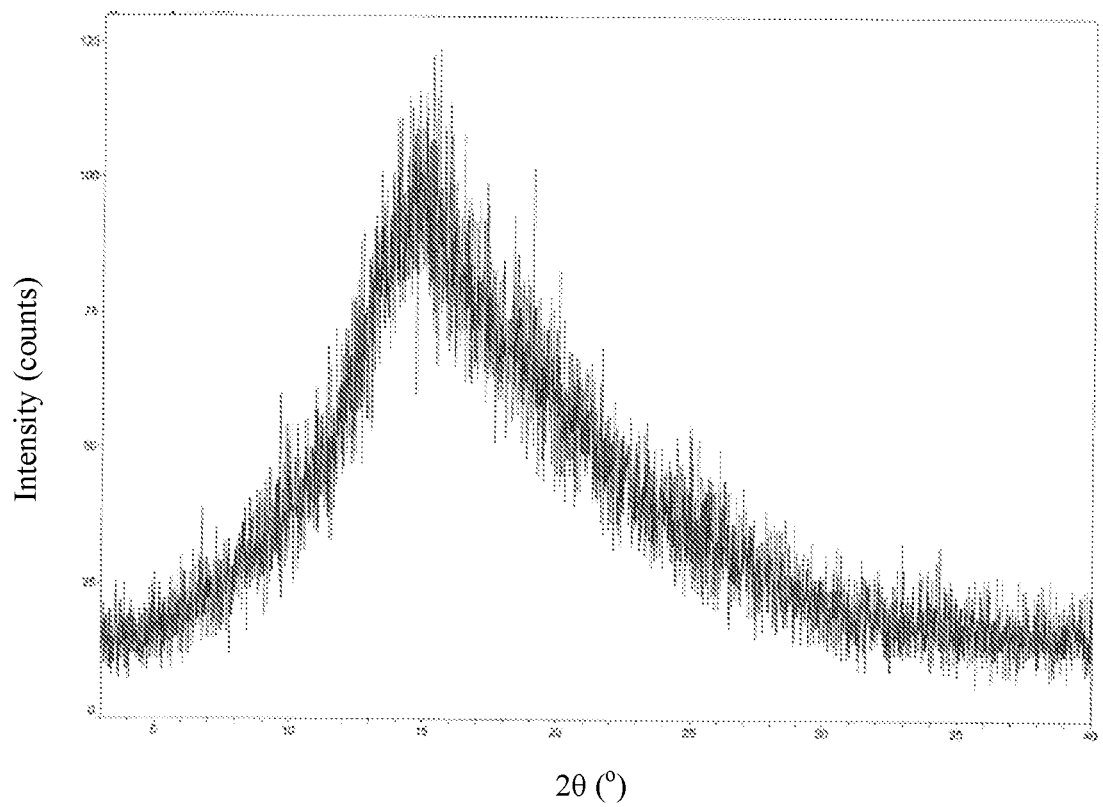
FIG. 5 is an X-ray powder diffraction pattern of amorphous powder of tenvermectin B obtained in Comparative Example 1.

Comparative Example 1: Preparation of Amorphous Powder of Tenvermectin B 5.0 g of tenvermectin B raw material (purity 98.2% by HPLC) was dissolved in 200 ml of ethanol solvent, and then filtered to obtain transparent filtrate. 800 ml of water were dropwisely added thereto in 20 minutes, thus obtained mixture was placed on a magnetic stirrer to stir at 200 r/min. After stirring at 25° C. for 10 h, the mixture was filtered to obtain a solid which was dried at 50° C. under vacuum for 48 h. The product was sampled for testing. X-ray powder diffraction pattern of the product was shown in FIG. 5 and showed that the sample was amorphous powder of tenvermectin B (purity 98.3% by HPLC).

Comparative Example 2: Preparation of Amorphous Tenvermectin B 1.0 g of tenvermectin B raw material (purity 98.2% by HPLC) was dissolved in 200 ml of ethyl acetate, and then 100 ml of hexene was added thereto. After being mixed evenly, thus obtained mixture was filtered to obtain transparent filtrate which was concentrated under vacuum at 50° C. to dryness. Thus obtained solid was dried under vacuum at 50° C. for 48 h. The obtained product was sampled for testing. Test result of the X-ray powder diffraction pattern of the product showed that the product was amorphous powder of tenvermectin B (purity 97.6% by HPLC). The X-ray powder diffraction pattern of the product was consistent with that of the amorphous tenvermectin B obtained in Comparative Example 1.

Stability Test 10 gram of the crystal form I of tenvermectin B obtained in Example 1 and 10 gram of the amorphous tenvermectin B obtained in Comparative Example 1 were taken and placed into double-layer PE bags by 1 g per bag. The bags were electrothermally sealed, and then placed into aluminum foil bags which were also electrothermally sealed. The sealed foil bags were placed at conditions of a temperature of 40±2° C. and a humidity of 75±5% for accelerated experiment, wherein, the amorphous tenvermectin B sample was degraded by 15% in the first month, while the crystal form I of tenvermectin B was basically stable after a storage of 6 months, and the data were shown in Table 2 below.

TABLE 2

Stability data of crystal form I of tenvermectin B

| Item | Initial data | First month | Second month | Third month | Sixth month |
| --- | --- | --- | --- | --- | --- |
| Appearance | White crystalline powder | White crystalline powder | White crystalline powder | White crystalline powder | White crystalline powder |

TABLE 2-continued

Stability data of crystal form I of tenvermectin B

| Item | Initial data | First month | Second month | Third month | Sixth month |
|---|---|---|---|---|---|
| XRPD | crystal form I | crystal form I | crystal form I | crystal form I | crystal form I |
| Purity by HPLC | 99.1 | 99.0 | 99.1 | 98.9 | 98.9 |

The invention claimed is:

1. A crystal form I of tenvermectin B, wherein the crystal form I of tenvermectin B exhibits characteristic peaks at 2θ degree of 4.63±0.20°, 6.71±0.20°, 9.22±0.20°, 9.62±0.20°, 11.33±0.20°, 11.79±0.20°, 12.02±0.20°, 12.48±0.20°, 13.48±0.20°, 14.95±0.20°, 15.45±0.20°, 15.80±0.20°, 16.64±0.20°, 17.39±0.20°, 17.74±0.20°, 18.33±0.20°, 19.20±0.20°, 19.75±0.20°, 21.12±0.20°, 22.14±0.20°, 22.52±0.20°, 22.97±0.20°, 23.70±0.20°, 25.01±0.20°, 25.54±0.20°, 26.53±0.20°, 27.16±0.20° and 29.60±0.20° in X-ray powder diffraction pattern using Cu-Kα radiation.

2. A composition containing the crystal form I of tenvermectin B according to claim 1.

3. A method for controlling parasites and harmful insects, comprising using effective amount of the crystal form I of tenvermectin B according to claim 1.

4. A method for preparing the crystal form I of tenvermectin B according to claim 1, wherein the method comprises a step of precipitating the crystal form I of tenvermectin B from a solvent system containing formamide;

wherein the solvent system containing formamide is a combination of ethanol, formamide and water or a combination of acetone, formamide and water;

the method comprises steps of: dissolving tenvermectin B with ethanol or acetone, then adding formamide and water in sequence, stirring and crystallizing the thus obtained mixture to obtain the crystal form I of tenvermectin B;

wherein a ratio of the mass of the tenvermectin B to the volume of ethanol or acetone to the volume of formamide to the volume of water is 1 g:2 ml:4-5 ml:2 ml.

* * * * *